United States Patent [19]

Schröeder

[11] 4,066,691
[45] Jan. 3, 1978

[54] PROCESS FOR THE PRODUCTION OF PURE DIGLYCOLIC ACID BY OXIDATION OF DIETHYLENE GLYCOL WITH NITRIC ACID

[75] Inventor: Manfred Schröeder, Marl, Germany

[73] Assignee: Chemische Werke Huels Aktiengesellschaft, Marl, Germany

[21] Appl. No.: 721,577

[22] Filed: Sept. 8, 1976

[30] Foreign Application Priority Data

Sept. 12, 1975 Germany ............................... 2540726

[51] Int. Cl.$^2$ ....................... C07C 51/26; C07C 51/42
[52] U.S. Cl. ................................................. 260/531 R
[58] Field of Search .................................... 260/531 R

[56] References Cited

U.S. PATENT DOCUMENTS 3,476,804   11/1969   Bende et al. ...................... 260/531 R

FOREIGN PATENT DOCUMENTS 2,206,862   8/1973   Germany ......................... 260/531 R Primary Examiner—Vivian Garner
Attorney, Agent, or Firm—Millen & White

[57] ABSTRACT

A process for the production of pure diglycolic acid by oxidation of diethylene glycol with nitric acid, comprises the steps of:

a. cooling the reaction mixture formed during the oxidation to a temperature of $-10°$ to $+25°$ C. and separating a first quantity of thus-crystallized diglycolic acid;

b. concentrating the first mother liquor at 5 – 530 millibars to a concentration of 35–45% by weight of $HNO_3$ and cooling to a temperature of $-10°$ to $+25°$ C.;

c. separating a further quantity of thus-crystallized diglycolic acid; and d. recycling the remaining second mother liquor to the reactor for oxidizing diethylene glycol with nitric acid.

9 Claims, 1 Drawing Figure

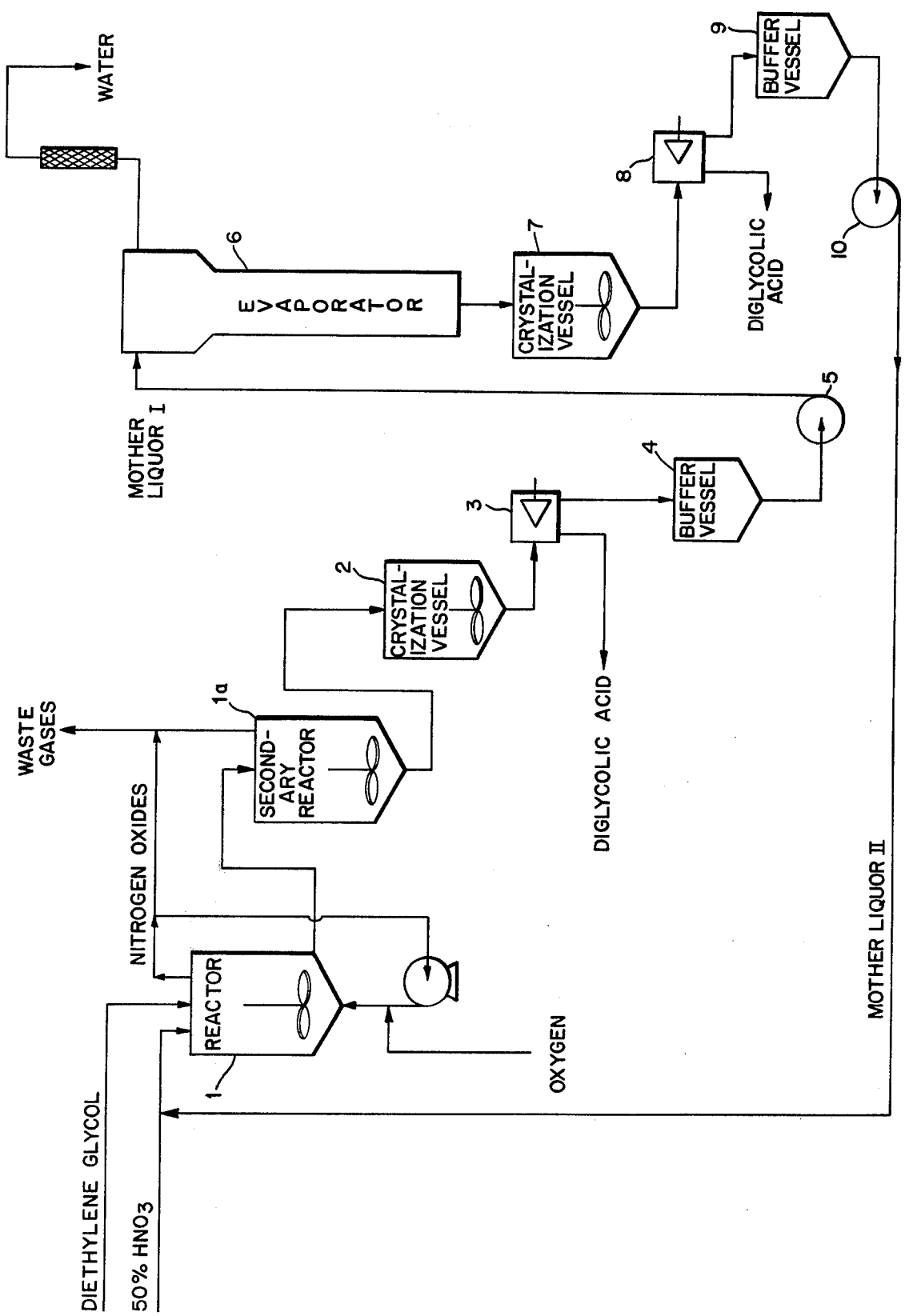

PROCESS FOR THE PRODUCTION OF PURE DIGLYCOLIC ACID BY OXIDATION OF DIETHYLENE GLYCOL WITH NITRIC ACID

BACKGROUND OF THE INVENTION

The production of diglycolic acid by oxidation of diethylene glycol with concentrated aqueous nitric acid is well known. Wurtz, Ann. Chimie [3], 69, 334, 342 (1863).

In a process for the production of ethylenebis (glycolic acid) disclosed in British Patent 639,491, triethylene glycol is gradually added to a 6-molar excess of concentrated, approximately 60% nitric acid at a temperature of 40°–90° C. Nitric acid concentration is maintained constant during the course of the reaction by addition of concentrated nitric acid.

The reaction of diethylene glycol with nitric acid takes place analogously. The process is carried out at the same temperatures; a nitric acid concentration of 35–65%, preferably 50–60%, is employed and a 0.4 – 16-molar excess of nitric acid is utilized. To improve utilization of the nitric acid, oxygen can be added to the reaction mixture to oxidize the thus-formed nitrogen oxides; any nitrogen oxides escaping from the reaction mixture are recycled into the latter. See, DOS's (German Unexamined Laid-Open Applications) 2,206,862 and 2,244,243.

After termination of the reaction, an aqueous reaction mixture, containing approximately 5–30% by weight of $HNO_3$ and about 20–40% by weight of diglycolic acid, in addition to minor proportions of impurities, such as oxalic acid and glycolic acid, is obtained. According to the state of the art this solution is worked up by evaporating all of the water and nitric acid under vacuum. The thus-separated diglycolic acid is recrystallized once more, if necessary.

However, industrial exploitation of such a process step is impractical, because the physical state of the reaction product changes from liquid phase to solid phase during the evaporation. Due to instability of the thus-separated molten diglycolic acid, it is impossible to discharge the acid as a liquid phase by heating the acid above its melting point. Furthermore, complete evaporation of water and nitric acid from the reaction product requires a high expenditure of energy.

Thus, there is a continuing need for a process in which complete evaporation of water and nitric acid, in the reaction product and the high energy consumption associated therewith can be avoided.

SUMMARY OF THE INVENTION

This invention relates, in a process for the production of pure diglycolic acid by oxidation of diethylene glycol with nitric acid in a reaction zone to form a reaction mixture containing diglycolic acid, to the improvement comprising:

a. cooling at least a portion of the reaction mixture to −10° to +25° C. to crystallize a portion of the diglycolic acid therein;

b. separating the crystallized diglycolic acid from the cooled reaction mixture;

c. concentrating the resultant mother liquor at 5–530 mb. to a nitric acid concentration of 35–45% by weight;

d. cooling the concentrated mother liquor to −10° to +25° C to crystallize a second portion of diglycolic acid, e. separating the second portion of crystallized diglycolic acid from the cooled mother liquor; and f. recycling the mother liquor to the zone for oxidation of diethylene glycol with nitric acid.

DETAILED DESCRIPTION

The process of this invention will be explained in greater detail with reference to the drawing.

The reaction of diethylene glycol with 50% aqueous nitric acid takes place in reaction zone or reactor 1, with recycling of nitrogen oxides and simultaneous addition of oxygen. To terminate the reaction, the reaction mixture is transferred into secondary reactor or reaction zone 1a. From the latter, the reaction mixture is introduced into the cooled crystallization vessel 2. Crystallized diglycolic acid is separated from the cooled mixture in filter unit 3. The first mother liquor thus obtained passes into buffer vessel 4 and is pumped from the buffer vessel into a vacuum thin-film evaporator 6 by a pump 5. In the evaporator, water is removed from the mother liquor. After the first mother liquor has been concentrated to the desired nitric acid concentration, it is passed to a second cooled crystallizing tank 7, from which precipitated diglycolic acid is discharged by a second filter unit 8. The mother liquor from the second crystallization is returned to reactor 1 via a buffer vessel 9 by a pump 10.

Depending on the crystallization temperature employed, 70–75% of the diglycolic acid in the reaction mixture leaving secondary reactor 1a is separated. The remaining diglycolic acid is recycled to main reactor 1, in solution, in the second mother liquor.

The separated diglycolic acid is obtained in extremely pure form. Any additional purification, such as, for example, recrystallization, is superfluous. After drying, practically 100% strength acid is obtained. Minimal amounts of impurities, such as oxalic acid, are dissolved in the mother liquor. Enrichment of impurities in the mother liquors can be prevented by discharging and purifying a partial stream of the second mother liquor returned to reaction 1.

The partial stream may be purified by evaporation of the nitric acid which is recycled, and the remaining solid residue can be recrystallized from appropriate solvents like acetone, methylethylketone or acetic acid.

Deviations from the scheme illustrated in the drawing are also possible. Filter unit 8 and be omitted, for example, and the concentrate obtained in crystallizing tank 7 can be conducted over filter unit 3. In this case, only a portion of the mother liquor going into buffer vessel 4 is transferred into thin-film evaporator 6. The rest of the mother liquor is transferred to reactor 1. The acid concentration of this mother liquor required for the oxidation reaction can be adjusted by adding concentrated nitric acid. However, this procedure is less advantageous than scheme above, because the separation rate is lower.

This practice os this invention permits very mild workup operation for reaction mixtures obtained by the oxidation, especially since a portion of the diglycolic acid product has already been separated in crystalline form by cooling prior to the step of concentrating by evaporation under vacuum. The diglycolic acid can be crystallized from the reaction mixture and from the concentrate of the first mother liquor by cooling to −10° to +25° C. With decreasing temperature, the amount of thus-crystallized diglycolic acid increases, but costs of refrigeration also increase. Very favorable results with reasonable expenses are obtained by cooling in the range of 0°-5° C.

Evaporation of the first mother liquor is conducted under vacuum, at a pressure of 5-530 mb. If the pressure rises above 530 mb., lower yields can result because of degradation phenomena in the mother liquor caused by the higher evaporation temperature required. Pressures below 5 mb. are difficult to attain. An especially preferred pressure range is between 50 and 200 mb.

The evaporation is advantageously conducted in a thin-film evaporator unit. The mother liquor is evaporated until $HNO_3$ content ranges between 35 and 45% by weight. If the value falls substantially below 35% by weight, the proportion of thus-crystallized diglycolic acid is reduced. If $HNO_3$ concentration rises considerably above 45% by weight, decreases in yield result due to a rise in oxidative degradation of the dissolved diglycolic acid.

During the evaporation step, the temperature is generally 25°-90° C., in the pressure range of 5-530 mb. In the preferred pressure range of 50-200 mb., the temperature will be 40°-60° C.

The process of this invention can be used in batch or continuous processes, but preferably is used in a continuous process in which nitric oxides and the second mother liquor are recycled to the reactor.

In a most preferred embodiment, the process outlined in the Summary, above, is carried out, with the proviso that said process is continuous, nitrogen oxides are recycled to said reaction zone and oxygen is added during the oxidation;

nitric acid used for oxidation of diethylene glycol in said reaction zone is maintained at 50-60% by weight of said reaction mixture;

the portion of said reaction mixture to be cooled is transferred to a secondary reaction zone prior to step (a);

said resultant mothor liquor from step (b) is concentrated in step (c) in a vacuum thin-film evaporator.

70-75% of diglycolic acid in said portion of said reaction mixture is crystallized and separated in steps (b) and (e).

The primary advantage of this invention is that the liquid phase, which is easily handled, is retained during evaporation of the reaction product. The hard-to-control transition from liquid to solid phase during the distillative workup operation is avoided. Furthermore, the energy requirement can be considerably reduced, since evaporation and condensation of unreacted nitric acid are eliminated.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

At a temperature of 70° C., reactor 1 is charged, per hour, with 1.3 1. of aqueous nitric acid ($HNO_3$ content 50% by weight), 0.4 1. of diethylene glycol, and 0.65 1. of second mother liquor returned from buffer vessel 9 and containing 12.3% by weight of diglycolic acid and 50.2% by weight of $HNO_3$. Nitrogen oxides formed during the reaction are recycled to the reaction mixture by a blower along with addition of 100 1. of oxygen per hour. The residence time of the reaction mixture in reaction vessels 1 and 1a is a total of 2.2 hours. The reaction solution leaving secondary reactor 1a has a composition of 23.5% by weight of $HNO_3$ and 27.2% by weight of diglycolic acid and passes into crystallizing vessel 2, which is cooled to 0° C. In filter unit 3, a first portion of 161 g. of diglycolic acid is separated. The first mother liquor flows into buffer vessel 4. From this buffer vessel, 2 1. of mother liquor is discharged per hour with a content of 24.5% by weight of $HNO_3$ and 21.5% by weight of diglycolic acid and passed into the thin-film evaporator 6. The wall temperature of the thin-film evaporator is 145° C.; the pressure is 100-120 mb. In the thin-film evaporator, the first mother liquor is stripped of 0.9 1. of water with a content of 0.1 - 0.3% by weight of $HNO_3$ per hour. The concentrated solution, amounting to 1.7 kg. per hour and containing 38.5% by weight of $HNO_3$ and 33.1% by weight of diglycolic acid, leaves the thin-film evaporator at a temperature of 50°-55° C. and passes to the crystallizer 7 cooled to 0° C. In the filter unit 8 disposed downstream thereof, another portion of 394 g. of thus-crystallized diglycolic acid is separated. The remaining second mother liquor in an amount of 0.6 - 0.7 1./h. contains 12.3% by weight of diglycolic acid and 50.2% by weight of $HNO_3$ and is returned to reactor 1.

The amount of diglycolic acid separated during the process in the two filter units and dried is 555 g. per hour, corresponding to a yield of 98%, based on the diethylene glycol employed. The purity of the diglycolic acid is practially 100%; the amount of nitrogen-containing impurities in the diglycolic acid is less than 0.01% (calculated as N).

EXAMPLE 2

Using the system described in Example 1, the following reaction conditions are maintained:

Reactor Feed:
0.7 1./h. 55% nitric acid
0.2 1./h. diethylene glycol (2.11 moles)
0.3 1./h. mother liquor II
(content: 43% by weight $HNO_3$ 16% by weight diglycolic acid)
50 1./h. oxygen The nitrogen oxides formed during the reaction are not recirculated but rather escape via the waste gas conduit.

Composition of the reaction mixture leaving the reactor 1a:
16.5% by weight $HNO_3$
34.1% by weight diglycolic acid Composition of mother liquor I after cooling (+2° C.) and separation of the crystallized diglycolic acid:
22.1% by weight $HNO_3$
22.5% by weight diglycolic acid Feed introduced into thin-film evaporator 6:
0.7 - 0.8 1./h. mother liquor I Discharge:
0.2 - 0.3 1./h. distillate (water)
0.5 1./h. concentrate Composition of the concentrate leaving the thin-film evaporator 6:
39.4% by weight of $HNO_3$
36.5% by weight of diglycolic acid Composition of the concentrate after cooling (+2° C.) and separation of the thus-crystallized diglycolic acid (mother liquor II):

43.0% by weight of HNO$_3$
16.0% by weight of diglycolic acid
Total yield of crystalline diglycolic acid:
280 g./h. (2.09 moles); yield = 99% of theory, based on diethylene glycol;
m.p. 142° C.;
purity practically 100%;
N-content: 0.001%

The preceding examples can be repreated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of pure diglycolic acid by oxidation of diethylene glycol with nitric acid in a reaction zone to form a reaction mixture containing diglycolic acid, the improvement comprising:
   a. cooling at least a portion of the reaction mixture to −10° to +25° C. to crystallize a portion of the diglycolic acid therein;
   b. separating the crystallized diglycolic acid from the cooled reaction mixture;
   c. concentrating the resultant mother liquor at 5–530 mb. to a nitric acid concentration of 35–45% by weight;
   d. cooling the concentrated mother liquor to −10° to +25° C. to crystallize a second portion of diglycolic acid;
   e. separating the second portion of crystallized diglycolic acid from the cooled mother liquor; and
   f. recycling the mother liquor to the reaction zone for oxidation of diethylene glycol with nitric acid.

2. The process of claim 1, wherein said portion of said reaction mixture is cooled to 0°–5° C and the mother liquor is concentrated at 50–200 mb and cooled at 0°–5° C.

3. The process of claim 1, wherein said process is continuous, nitrogen oxides produced during the oxidation are recycled to said reaction zone and oxygen is added during the oxidation.

4. The process of claim 1, wherein nitric acid used for oxidation of diethylene glycol in said reaction zone is maintained at 35–65% by weight of said reaction mixture.

5. The process of claim 1, wherein the portion of said reaction mixture to be cooled is transferred to a secondary reaction zone prior to step (a).

6. The process of claim 1, wherein said resultant mother liquor from step (b) is concentrated in step (c) in a vacuum thin-film evaporator.

7. The process of claim 1, wherein 70–75% of diglycolic acid in the portion of said reaction mixture is crystallized and separated in steps (b) and (e).

8. The process of claim 1, wherein said process is continuous, nitrogen oxides produced during the oxidation are recycled to said reaction zone and oxygen is added during the oxidation;
   nitric acid used for oxidation of diethylene glycol in said reaction zone is maintained at 50–60% by weight of said reaction mixture;
   the portion of said reaction mixture to be cooled is transferred to a secondary reaction zone prior to step (a);
   said resultant mother liquor from step (b) is concentrated in a vacuum thin-film evaporator; and
   70–75% of diglycolic acid in said portion of said reaction mixture is crystallized and separated in steps (b) and (e).

9. The process of claim 8, wherein said portion of said reaction mixture is cooled to 0°–5° C. and said resultant mother liquor after removal of crystallized diglycolic acid therefrom is concentrated at 50–200 mb. and then cooled to 0°–5° C. to crystallize the second portion of diglycolic acid therefrom.

* * * * *